United States Patent [19]

Oguro et al.

[11] Patent Number: 4,954,512
[45] Date of Patent: * Sep. 4, 1990

[54] ANTI-ULCER COMPOSITION

[75] Inventors: Katsunori Oguro; Hiroshi Nojima; Nobuyuki Hashizume; Norio Ohno; Taketoshi Naito, all of Tokyo, Japan

[73] Assignees: Shosuke Okamoto, Hyogo; Showa Denko Kabushiki Kaisha, Tokyo, both of Japan

[*] Notice: The portion of the term of this patent subsequent to Oct. 10, 2006 has been disclaimed.

[21] Appl. No.: 275,193

[22] Filed: Nov. 23, 1988

[30] Foreign Application Priority Data

Nov. 24, 1987 [JP] Japan .................. 62-297082

[51] Int. Cl.$^5$ .................. A61K 31/44; A61K 31/16; A61K 31/24; A61K 31/195
[52] U.S. Cl. .................. 514/352; 514/535; 514/538; 514/539; 514/542; 514/563; 514/616; 514/620; 514/925; 514/926; 514/927
[58] Field of Search .................. 514/620, 352, 925, 926, 514/927, 535, 538, 539, 542, 563, 616; 564/157

[56] References Cited

PUBLICATIONS

Chemical Abstracts vol. 109(9) 73913d (1988).
Chemical Abstracts vol. 108(11) 94946m (1988).
Chemical Abstracts vol. 104(18) 155980j (1986).
Chemical Abstracts vol. 100(1) 7165z (1984).
Chemical Abstracts vol. 74(1) 3865z (1971).
Chem. Abstracts vol. 107:78250d (1987).

Primary Examiner—Douglas W. Robinson
Attorney, Agent, or Firm—Sughrue, Mion, Zinn, Macpeak & Seas

[57] ABSTRACT

An anti-peptic ulcer composition containing, as an active ingredient, a therapeutically effective amount of a compound having the formula (I):

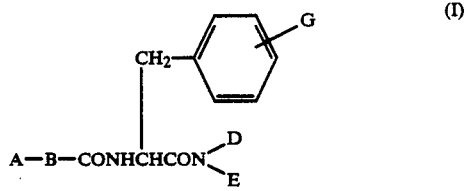

(I)

wherein A represents $H_2NCH_2-$,

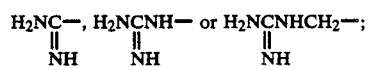

B represents

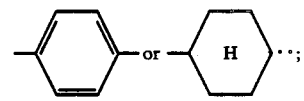

D and E each independently represent H, R, $-R'CO_2R-$, $-R'(OH)CO_2R$,

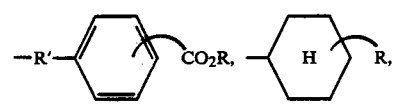

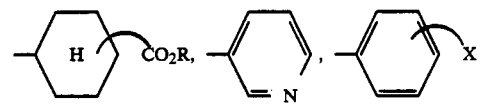

wherein X represents H, $CONR_2$, CONHR, $CONH_2$, $CO_2H$, $CO_2R$, or COR or $-R'(CO_2R)-$; R' represents a lower alkylene group and R represents a lower alkyl group; F represents H,

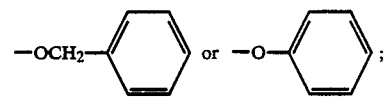

or a pharmaceutically acceptable salt thereof, and a pharmaceutically acceptable carrier.

9 Claims, No Drawings

ANTI-ULCER COMPOSITION

BACKGROUND OF THE INVENTION

1. Field of the Invention

The present invention relates to an anti-peptic ulcer composition.

2. Description of the Related Art

The causes of a peptic ulcer are generally considered to be an upset of the balance between an offense factor and a defense factor, on the basis of the theory of Shay and Sun (1963).

More specifically, this theory postulates that an ulcer will be formed when the balance between the offense factors acting on digestive mucosa to form an ulcer (acid, pepsin, etc.) and the defense factors having an anti-ulcer effect (mucus, mucosa, blood stream, prostaglandin, etc.) is upset and the offense factors become more preferential.

Accordingly, the anti-peptic ulcer therapeutical agents have been broadly classified into offense factor inhibitors and defense factor potentiators, in accordance with the above theory, and many drugs therefore have been developed and used.

As the offense factor inhibitors, histamine $H_2$ receptor antagonists having a potent gastric acid secretion inhibiting activity are widely used, as represented by drugs such as Cimetidine, Lanitidine, and Phamotidine. Also, Omeplasol, which is a proton pump inhibitor having a more potent gastric acid secretion inhibiting activity, has been developed.

On the other hand, as the defense factor potentiators, Gefalnate and Squralfate, which burst, protect and remedy gastric mucosa, Aldioxa and Glycyrrhizin, which are granulation neoplastic promoters and Cetraxate and Sophalcon, which are minute circulation ameliorators, are known. Also, Misoprostol, which is a $PGE_1$ preparation of prostaglandin (PG) derivatives physiologically active in the living body having cytoprotection, and Ornoprosteyl, which is a $PGE_2$ preparation, are known.

Nevertheless, partly because the various factors for ulcer formation have a complicated relationship to the specificity of a disease, many anti-peptic ulcer agents do not have a satisfactory effect and safety.

For example, a histamine $H_2$ receptor antagonist has a potent gastric acid excretion inhibiting activity, which brings about a rapid amelioration of a disease and shortens the therapy time, and is currently used as a first selected drug. Nevertheless, a problem exists in that this drug increases the rate of recurrence of the disease after therapy. The causes of this recurrence seem to be an acid rebound, a lowered defense factor, and a distortion of tissue after restoration based on the rapid therapy. Also, in the case of Cimetidine, adverse reactions such as abnormality of endocrine glands, for example, gynecomastia, and psychological disorder such as disorientation, have been reported. Furthermore, offense factor inhibitors, which lower the acidity in the stomach over a long term, are thought to cause a nitrosoamine synthesis through bacteria, and thus the possibility exists of a carcinogenicity caused thereby.

Offense factor inhibitors including proton pump inhibitors have been assessed as symptomatic treatment agents which are gastric acid secretion inhibitors.

On the other hand, defense factor potentiators may be considered as substantive treatment agents than offense factor inhibitors. The drugs which have been developed do not have a sufficient cytoprotection effect and a drug having a potent therapeutical activity cannot be found. Also, PG preparations now under development are reported to have adverse effects such as diarrhea, miscarriages, etc., because physiologically active substances are administered.

Therefore, under the present situation, it is difficult to treat a peptic ulcer with only a defense factor potentiator, and thus mainly a combined therapeutical method using the above histamine $H_2$ receptor antanosist is employed.

In the internal treatment of ulcers, policies will change from a "quicker treatment" to a "cleaner treatment", from "a treatment of an ulcer during a disease" to a "prevention of a recurrence", and from "a uniform treatment" to an individual treatment corresponding to a specific disease".

Currently, the most desirable drug, from the viewpoint of the above trends, is a defense factor potentiator closer to the causative therapeutical method, but such a drug having a high effectiveness and low toxicity has not been found.

An object of the present invention is to provide a novel pharmaceutics having a cytoprotection effect providing a more substantial therapy.

SUMMARY OF THE INVENTION

Accordingly, the objects of the present invention are to eliminate the above-mentioned disadvantages of the prior art and to provide an anti-peptic ulcer composition effective for the therapy of a peptic ulcer.

Other objects are advantages of the present invention will be apparent from the following description.

In accordance with the present invention, there is provided an anti-peptic ulcer composition comprising a therapeutically effective amount of a compound represented by the formula (I) or a pharmaceutically acceptable salt thereof, as an active ingredient,

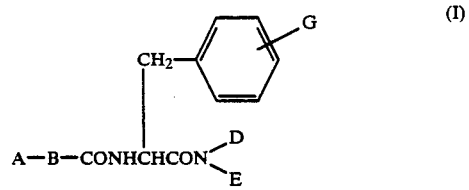

wherein A represents $H_2NCH_2-$,

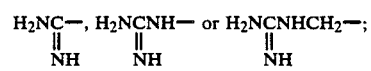

B represents

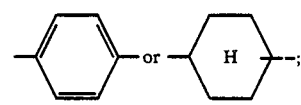

D and E each represent H, R, $-R'CO_2R$, $-R'(OH)CO_2R$,

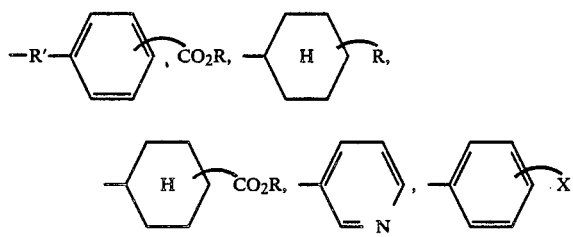

X represents H, CONR₂, CONHR, CONH₂, CO₂H, CO₂R, or COR or —R'(CO₂R)—; R' represents a lower alkylene group and R represents a lower alkyl group; G represents H,

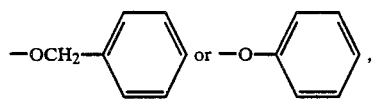

and a pharmaceutically acceptable carrier.

DESCRIPTION OF THE PREFERRED EMBODIMENTS

Examples of the pharmacologically acceptable salts are inorganic salts such as hydrochloride, hydrobromide, hydroiodide, sulfate, nitrate, and phosphate, and organic acid salts such as oxalate, succinate, glycolate, malate, citrate, maleate, lactate, benzenesulfonate, toluenesulfonate, and methanesulfonate.

Representative examples of the compounds represented by the above formula (I) are shown in Table 1.

The compounds shown in Table 1 are numbered, and in the following description, the individual compounds are represented, for convenience, by those compound numbers.

In the structural formula of the compound, (L) shows that the carbon thereof is L-isomer, and (DL) shows that the carbon thereof is DL-isomer. Note, the asymmetric carbon on the phenylalanine skelton is always L-isomer, unless otherwise stated.

The term NMR in the physical properties column denotes the nuclear magnetic resonance spectrum, and the numerals are δ (delta) values conventionally used to represent chemical shifts, with all units in ppm. As the solvent, CDCl₃ (deuterium chloroform) and CD₃OD (deuterium methanol) were used, and as the internal reference, TMS (tetramethylsilane) was used. The numerals represented in the brackets next to the δ values are the numbers of hydrogen, and in the representations subsequent thereto, n means singlet, d denotes doublet, t denotes triplet, q denotes quartet, m denotes multiplet, and broad denotes broad absorption peaks. The absorption peaks derived from the solvent were omitted.

The term IR denotes the IR-absorption spectrum, and was measured as a potassium bromide tablet unless otherwise particularly noted. The numerals show wave numbers in units of cm⁻¹. Note, only main absorption peaks are shown.

The term MS denotes the mass spectrum, and the numerals show the mass of a cation fragment divided by the charge M/e. Note, only main peaks are shown.

In the Table, (FAB) means a fast atom bombard method, and unless otherwise noted, the other results were measured by the electron ionization method.

TABLE 1

| No. | Compound | Physical Properties | |
|---|---|---|---|
| 1 | H₂NCH₂—⟨⟩⟍⟍⟍CONHCHCONH₂ with CH₂—phenyl side chain .HCl | NMR: CD₃OD, TMS δ: 0.84~2.26(10H, m) 2.74~2.92(3H, m) 3.12~3.21(1H, m) 4.57~4.65(1H, m) 7.10~7.32(5H, m) | IR: 3400, 3300, 3200, 2940, 1680, 1630, 1540, 1510, 1280, 1220 |
| 2 | H₂NCH₂—⟨phenyl⟩—CONHCHCONH₂ with CH₂—phenyl side chain .HCl | NMR: CD₃OD, TMS δ: 3.00~3.35(2H, m) 4.08~4.22(2H, broad S) 4.81~4.90(1H, m) 7.07~7.83(9H, m) | |
| 3 | H₂NCH₂—⟨⟩⟍⟍⟍CONHCHCONH—⟨phenyl-CO₂C₂H₅⟩ with CH₂—phenyl side chain .HCl | NMR: CD₃OD, TMS δ: 0.92~2.40(13H, m) 2.72~3.00(3H, m) 3.38~3.48(1H, m) 4.33(2H, q) 4.67~4.74(1H, m) 7.10~7.28(6H, m) 7.52~7.60(1H, m) 8.00~8.08(1H, m) 8.60~8.65(1H, m) | |

TABLE 1-continued

| No. | Compound | Physical Properties | |
|---|---|---|---|
| 4 | 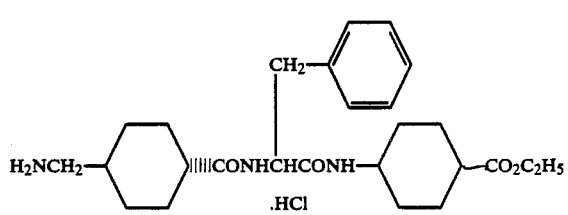 | NMR:<br>CD$_3$OD, TMS<br>δ: 0.82~2.52(19H, m)<br>2.76~3.08(4H, m)<br>3.60~3.77(1H, m)<br>4.11(2H, q)<br>4.52~4.61(1H, m)<br>7.08~7.28(5H, m) | |
| 5 | 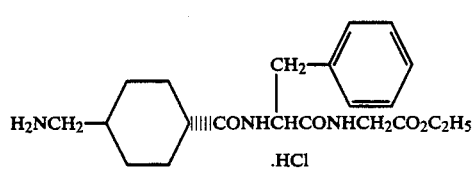 | NMR:<br>CD$_3$OD, TMS<br>δ: 0.84~2.24(13H, m)<br>2.68~2.91(3H, m)<br>3.15~3.22(1H, m)<br>3.92(2H, s)<br>4.16(2H, q)<br>4.64~4.72(1H, m)<br>7.08~7.27(5H, m) | IR:<br>3300, 2940, 1740,<br>1640, 1550, 1220,<br>1200, 1020 |
| 6 | 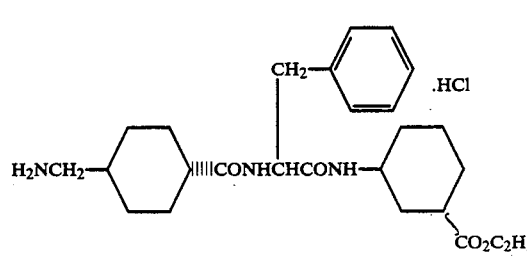 | NMR:<br>CD$_3$OD, TMS<br>δ: 0.76~2.44(19H, m)<br>2.74~3.07(3H, m)<br>3.53~3.64(1H, m)<br>4.03~4.17(2H, m)<br>4.43~4.55(1H, m)<br>7.08~7.18(5H, m) | IR:<br>3300, 2940, 1735,<br>1640, 1550, 1530,<br>1215 |
| 7 | 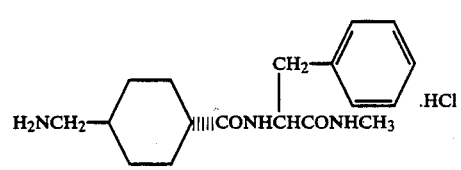 | NMR:<br>CD$_3$OD, TMS<br>δ: 0.86~2.27(10H, m)<br>2.69(3H, s)<br>2.74~2.90(3H, m)<br>3.06~3.15(1H, m)<br>4.49~4.58(1H, m)<br>7.11~7.32(5H, m) | |
| 8 | 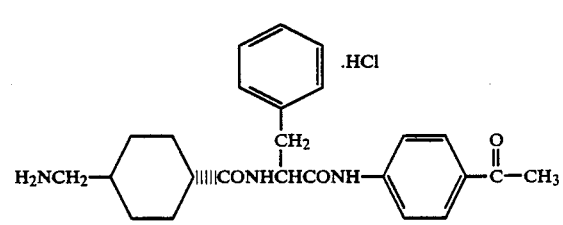 | | NMR:<br>CD$_3$OD, TMS<br>δ: 0.90~1.96(9H, m)<br>2.15~2.36(1H, m)<br>2.56(3H, s)<br>2.78(2H, d)<br>2.93~3.23(2H, m)<br>4.71~4.79(1H, m)<br>7.10~7.32(5H, m)<br>7.56~7.96(4H, m) |
| 9 | 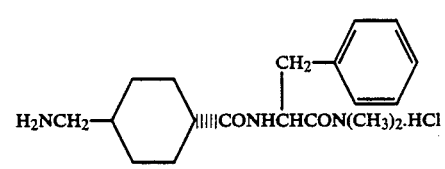 | NMR:<br>CD$_3$OD, TMS<br>δ: 0.84~2.31(10H, m)<br>2.76~3.18(10H, m)<br>4.98~5.05(1H, m)<br>7.08~7.28(5H, m) | IR:<br>3375, 2940, 1645,<br>1638, 1530 |
| 10 | 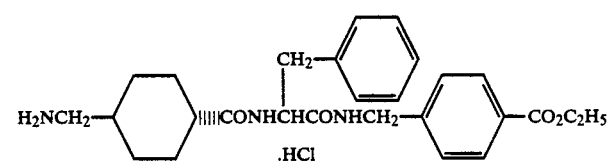 | NMR:<br>CD$_3$OD, TMS<br>δ: 0.83~2.34(13H, m)<br>2.70~3.19(4H, m)<br>4.31~4.43(4H, m)<br>4.61~4.70(1H, m)<br>7.11~7.31(7H, m)<br>7.95(2H, d) | |

TABLE 1-continued

| No. | Compound | Physical Properties | |
|---|---|---|---|
| 11 | H₂NCH₂–[cyclohexyl]–CONHCH(CH₂Ph)CO–N[piperidine]–CO₂C₂H₅ · HCl | NMR:<br>CD₃OD, TMS<br>δ: 0.92~2.41(18, m)<br>2.60~3.08(4H, m)<br>3.76~4.25(6H, m)<br>4.98~5.12(1H, m)<br>7.10~7.33(5H, m) | |
| 12 | HN=C(NH₂)–NH–C₆H₄–CONHCH(CH₂Ph)CONH–[cyclohexyl]–CH₃ · HCl | MS:<br>M/c 379, 288, 266,<br>244, 240, 224,<br>136, 120, 99 | NMR:<br>CD₃OD, TMS<br>δ: 0.52~1.90(11H, m)<br>2.92~3.88(6H, m)<br>4.24~4.76(1H, broad)<br>6.96~7.60(4H, m)<br>8.08~8.80(2H, broad) |
| 13 | H₂NCH₂–[cyclohexyl]–CONHCH(CH₂Ph)CONH–C₆H₄–CONH₂ · HCl | NMR:<br>CD₃OD, TMS<br>δ: 0.88~2.34(10H, m)<br>2.77(2H, d)<br>2.93~3.23(2H, m)<br>4.71~4.79(1H, m)<br>7.08~7.30(5H, m)<br>7.59~7.85(4H, m) | IR:<br>3360, 3320, 3200,<br>2940, 1680, 1645,<br>1610, 1530, 1415,<br>1397 |
| 14 | H₂NCH₂–[cyclohexyl]–CONHCH(CH₂Ph)CONH–C₆H₄–CO₂H · HCl | NMR:<br>CD₃OD, TMS<br>δ: 0.87~2.31(10H, m)<br>2.70~2.80(2H, m)<br>2.91~3.22(2H, m)<br>4.69~4.79(1H, m)<br>7.08~7.32(5H, m)<br>7.56~7.96(4H, m) | |
| 15 | H₂NCH₂–[cyclohexyl]–CONHCH(CH₂Ph)CONHC(CH₃)₃ · HCl | NMR:<br>CD₃OD, TMS<br>δ: 0.90~2.29(10H, m)<br>1.24(9H, s)<br>2.74~3.07(4H, m)<br>4.47~4.56(1H, m)<br>7.12~7.30(5H, m) | |
| 16 | H₂NCH₂–C₆H₄–CONHCH(CH₂Ph)CONH–C₆H₄–CO–CH₃ · HCl | IR:<br>3430, 3030, 2930,<br>1670, 1640, 1630,<br>1600, 1500, 1410,<br>1360, 1310, 1270,<br>1180 | NMR:<br>CD₃OD, TMS<br>δ: 2.56(3H, s)<br>3.10~3.30(2H, m)<br>4.16(2H, s)<br>4.90~5.0(1H, m)<br>7.10~8.0(13H, m) |
| 17 | H₂NCH₂–C₆H₄–CONHCH(CH₂Ph)CON(CH₃)₂ · HCl | IR:<br>3350, 2900, 1640,<br>1540, 1280, 1130,<br>1080, 840, 740,<br>690 | MS(FAB)<br>M/c: 326, 281,<br>253, 192,<br>134, 118,<br>105 |

TABLE 1-continued

| No. | Compound | Physical Properties | |
|---|---|---|---|
| 18 | 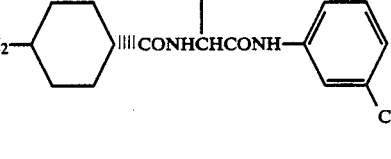 | NMR:<br>CD₃OD, TMS<br>δ: 0.88~2.32(13H, m)<br>2.87(2H, d)<br>2.92~3.22(2H, m)<br>4.34(2H, q)<br>4.68~4.76(1H, m)<br>7.12~7.41(6H, m)<br>7.64~7.74(2H, m)<br>8.12~8.19(1H, m) | |
| 19 | 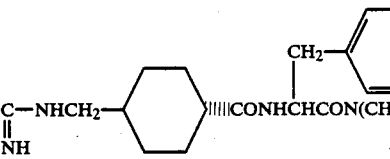 | IR:<br>2920, 1640, 1540,<br>1450, 1330, 1200,<br>1040, 780 | MS(FAB)<br>M/c: 374, 253,<br>182, 154,<br>120 |
| 20 | 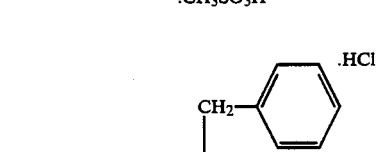 | NMR:<br>CD₃OD, TMS<br>δ: 0.88~2.28(13H, m)<br>2.72~2.95(3H, m)<br>3.17~3.28(1H, m)<br>2.76~2.95(2H, m)<br>4.19(2H, q)<br>4.44~4.52(1H, m)<br>4.64~4.76(1H, m)<br>7.12~7.28(5H, m) | IR:<br>3300, 2940, 1740,<br>1640, 1545, 1220,<br>1055 |
| 21 | 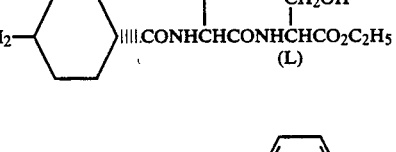 | NMR:<br>CD₃OD, TMS<br>δ: 0.88~2.36(13H, m)<br>2.71~2.80(2H, m)<br>2.92~3.23(2H, m)<br>4.33(2H, q)<br>4.70~4.80(1H, m)<br>7.08~7.22(5H, m)<br>7.56~7.97(4H, m) | IR:<br>3300, 2940, 1720,<br>1645, 1603, 1535,<br>1280, 1175, 1105 |
| 22 | 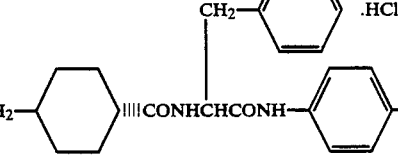 | NMR:<br>CD₃OD, TMS<br>δ: 2.87~2.95(6H, m)<br>3.10~3.18(2H, m)<br>5.19~5.30(1H, m)<br>7.16~7.36(5H, m)<br>7.80~8.03(4H, m) | |
| 23 | 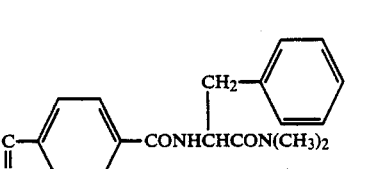 | NMR:<br>CD₃OD, TMS<br>δ: 0.88~2.33(10H, m)<br>2.72~2.83(2H, m)<br>2.90(3H, s)<br>2.93~3.24(2H, m)<br>4.69~4.79(1H, m)<br>7.08~7.30(5H, m)<br>7.56~7.77(4H, m) | |
| 24 | 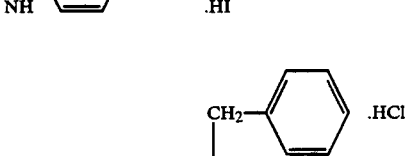 | NMR:<br>CD₃OD, TMS<br>δ: 0.88~2.36(10H, m)<br>2.70~3.28(10H, m)<br>4.70~4.80(1H, m)<br>7.12~7.32(5H, m)<br>7.37~7.70(4H, m) | |

| No. | Compound | Physical Properties | |
|---|---|---|---|
| 25 | H₂NCH₂—[cyclohexane]—||||CONHCHCON(CH₃)CH₂CO₂C₂H₅ with CH₂—[phenyl] ·HCl | NMR:<br>CD₃OD, TMS<br>δ: 0.88~2.28(13H, m)<br>2.70~3.20(7H, m)<br>4.10~4.36(4H, m)<br>5.05~5.16(1H, m)<br>7.10~7.30(5H, m) | |
| 26 | H₂NCH₂—[cyclohexane]—CONHCHCONH—[phenyl]—CONH₂ with CH₂—[phenyl] ·HCl | IR<br>3400, 3280, 3060,<br>2930, 2860, 1660,<br>1610, 1585, 1550,<br>1445, 1390, 1250,<br>1115, 1075, 870,<br>695 | |
| 27 | H₂NCH₂—[phenyl]—CONHCHCONH—[phenyl]—CONH₂ with CH₂—[phenyl] ·HCl | IR:<br>3400, 1640, 1600,<br>1540, 1410, 1250,<br>1110, 870, 690 | |
| 28 | H₂N—C(=NH)—[phenyl]—CONHCHCONH—[phenyl]—CONH₂ with CH₂—[phenyl], ·CH₃SO₃H | IR:<br>3375, 33, 3200,<br>1680, 1655, 1640,<br>1525, 1408, 1300 | |
| 29 | HN=C(NH₂)—[phenyl]—CONHCHCONH—[phenyl]—C(O)—CH₃ with CH₂—[phenyl] ·HI | IR:<br>3300, 3210, 2960,<br>2930, 2870, 1648,<br>1638, 1535, 1480,<br>1415, 1245, 1015,<br>885, 860 | |
| 30 | H₂NCH₂—[cyclohexane]—||||CONHCHCONHCH₂CH₂CO₂C₂H₅ with CH₂—[phenyl] ·HCl | NMR:<br>CD₃OD, TMS<br>δ: 0.80~2.26(10H, m)<br>1.24(3H, t)<br>2.32~2.48(2H, m)<br>2.70~3.14(4H, m)<br>3.30~3.45(2H, m)<br>4.10(2H, q)<br>4.48~4.58(1H, m)<br>7.10~7.28(5H, m) | |
| 31 | H₂NCH₂—[cyclohexane]—||||CONHCHCONH—[pyridyl] with CH₂—[phenyl-OCH₂-phenyl] ·2HCl | IR:<br>3650~2250, 1700,<br>1640, 1610, 1545,<br>1510, 1450, 1380,<br>1240, 1010, 800 | NMR:<br>CD₃OD, TMS<br>δ: 0.90~2.00(9H, m)<br>2.20~2.40(1H, m)<br>2.78(2H, d)<br>2.90~8.20(2H, m)<br>4.68(1H, m)<br>5.02(2H, s)<br>6.84~7.40(9H, m)<br>8.00(1H, m)<br>8.44~8.60(2H, m)<br>9.32(1H, s) |

TABLE 1-continued

| No. | Compound | Physical Properties |
|-----|----------|---------------------|
| 32 | 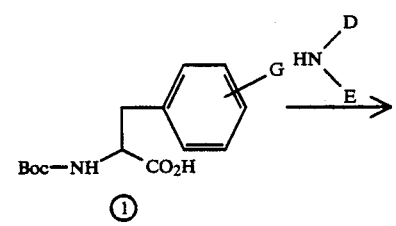 | NMR:<br>CD$_3$OD, TMS<br>δ: 0.80~2.32(10H, m)<br>2.50(3H, s)<br>2.78(2H, d)<br>2.90~3.30(2H, m)<br>4.70~4.82(1H, m)<br>6.76~7.96(13H, m) |

The reactions to be used for obtaining the compounds of the present invention are primarily the peptide syntheses, which comprise the introduction of a protective group, a peptide bond formation, and a protective group elimination, etc.

The known peptide bond formation reactions include the following methods.

(1) The mixed acid anhydride method:
   [Ann. Chem., 572, 190 (1951)]
(2) The acid chloride method:
   [Biochemistry, 4, 2219 (1965)]
(3) The phosphazo method:
   [Chem. Ber., 93, 2387 (1960)]
(4) The carbodiimide method:
   [J. Am. Chem. Soc., 77, 1067 (1955)]
   [J. Am. Chem. Soc., 84, 4457 (1962)]
   [Biochem, Biophy, Res. Comm., 52, No. 3 (1973)]
   [Chem. Ber., 103, 2034, (1970)]
   [Tetrahedron Lett., 46, 4475 (1978)]
(5) The activated ester method (e.g. the method using N-hydroxysuccinimide):
   [J. Am. Chem. Soc., 85, 3039 (1963)]

In the following description, use is made of representative examples of general reaction routes, but the peptide bond formation methods described are those (1) and (4). These, however, are not particularly limited when obtaining the compounds of the present invention. Various protective groups and the methods of introducing and removing such groups are described, and any thereof can be selected and used when obtaining the compounds of the present invention.

The general reaction routes for obtaining the compounds of the present invention are shown by the reaction routes (1), (2), and (3).

Reaction route 1) (wherein A denotes NH$_2$CH$_2$—)

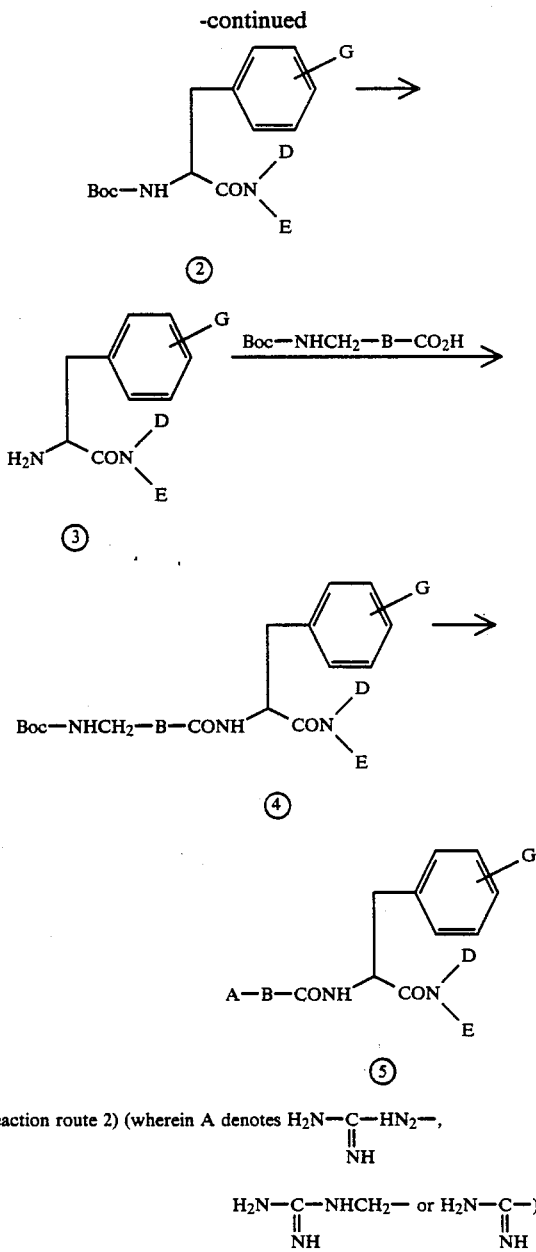

Reaction route 2) (wherein A denotes 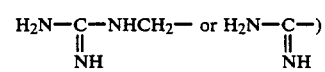

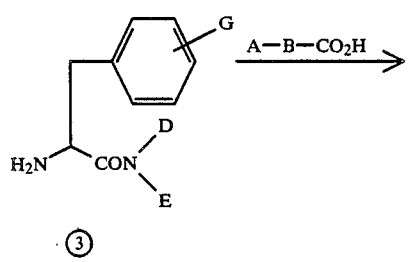

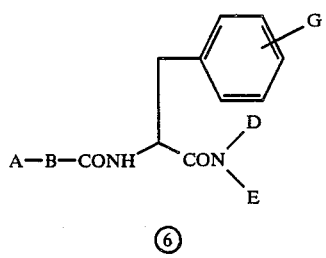

Reaction route 3) (wherein A denotes $H_2N-\underset{\underset{NH}{\|}}{C}-$)

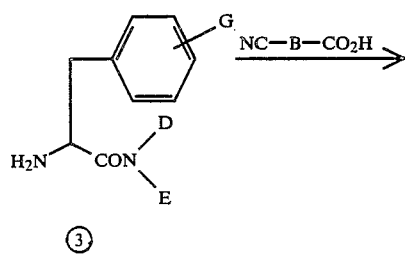

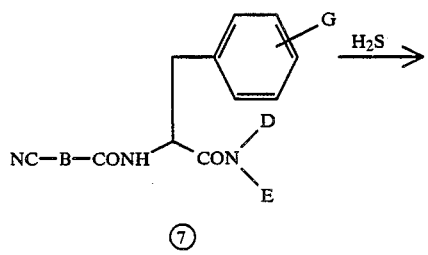

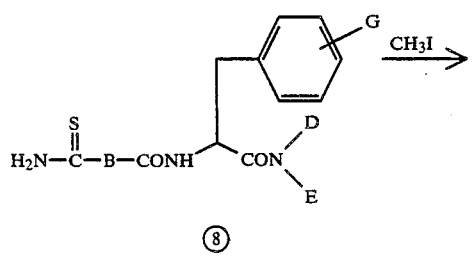

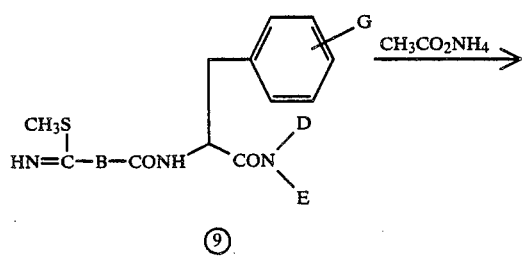

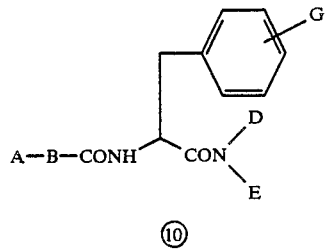

In the above formula (I), when A is $H_2NCH_2-$, it can by synthesized by the reaction route (1), and when A is

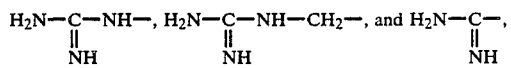

it can be synthesized by the reaction route (2). When A is

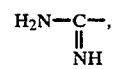

the compound also can be synthesized by the reaction route (3).

For the reacvions ① and ②, the mixed acid anhydride method or the carbodiimide method can be utilized.

In the mixed acid anhydride method, ① is dissolved in an appropriate solvent such as tetrahydrofuran, diethyl ether, dioxane, or N,N-dimetylformamide, and an appropriate base such as triethylamine or N-methylmorpholine is added in an amount of 1 to 5 equivalents, preferably 1 to 2 equivalents, based on 1. A chlorocarbonic acid ester is added to the reaction mixture as such or as a solution dissolved in the solvent used for the reaction, at one time or as several portions. At this time, the reaction mixture is maintained at a temperature of $-10°$ C. to $10°$ C., preferably $-5°$ C. to $5°$ C. The reaction time is preferably from 10 minutes to 3 hours, more preferably 15 minutes to one hour. After a conventional treatment, 0.5 to 2 equivalents of

are added, and the reaction is carried out at $-10°$ C. to $30°$ C., preferably $-5°$ C. to $20°$ C., for one hour to 50 hours, preferably 2 hours to 20 hours, and after completion of the reaction, the solids are collected by filtration or the reaction mixture as such is concentrated under a reduced pressure and the residue is extracted with an appropriate solvent such as diethyl ether, ethylacetate, dichloromethane, or chloroform to remove unreacted carboxylic acid and amines. After drying, the solvent is evaporated and the residue is purified by recrystallization or column chromatography to obtain ②.

In the carbodiimide method, a carbodiimide derivative, for example, 1,3-dicyclohexyl-carbodiimide, 1-ethyl-3-(3-dimethylaminopropyl) carbodiimide hydrochloride or the like in an amount of 1 to 5, preferably 1 to 2 equivalents based on ①, and

in an amount of 1 to 5 equivalents, preferably 1 to 3 equivalents based on ①, is added together with ① to a solvent, at 0° C. to room temperature, and the mixture is left to stand at 0° C. to room temperature for 1 hour to 24 hours. As the solvent, dry dichloromethane, chloroform, acetonitrile, 1,4-dioxane or pyridine may be employed. After completion of the reaction, the precipitates are removed, or when there is no precipitate, the reaction mixture as such is extracted with an appropriate solvent such as diethyl ether, ethyl acetate, dichloromethane, or chloroform and purified by a method similar to the mixed acid anhydride method to obtain ②.

By carrying out the reaction from ③ to ④, the reactions from ③ to ⑥ in the reaction route (2), and the reactions from ③ to ⑦ in the reaction route (3) by either one of the methods as described above, ④, ⑥ and ⑦ can be obtained respectively.

The reaction from ② to ③ can be carried out by adding a 4 N-HCl/dioxane solution to ② in an amount of 1 to 30 equivalents, preferably 5 to 20 equivalents based on ② followed by a reaction under room temperature. After completion of the reaction, a non-polar solvent such as hexane, pentane, heptane, or diethyl ether is added and the precipitated crystals are collected by filtration, or the solvent is evaporated under a reduced pressure, to obtain the hydrochloride of ③ as the residue.

The reaction from ③ to ④ can also be conducted in the same way as the reaction from ① to ② to give ④

The reaction from ④ to ⑤ can also be conducted in the same way as the reaction from ② to ③ to give ⑤

Synthesis of ⑦ to ⑩ in the reaction route (3) are performed as by the [Synthetic Method 19, 378].

The compound ① wherein G is 3-phenoxy, namely, N-(t-butoxycarbonyl)-3-phenoxy-DL-phenylalanine, is a novel compound, and therefore, the method of synthesizing same is described in detail in the Examples.

EXAMPLES

The present invention will now be further illustrated by, but is by no means limited to, the following Examples. In the following, the preparation of typical compounds is described by referring to specific examples.

EXAMPLE 1

Synthesis of
N-[trans-4-aminomethylcyclohexyl-carbonyl]-L-phenylalanine amide hydrochloride (Compound 1)

To a solution of trans-4-(t-butoxycarbonylaminomethyl)cyclohexyl carboxylic acid (3.86 g) dissolved in dry tetrahydrofuran (150.00 ml), triethylamine (2.25 ml) was added under ice-cooling and the mixture was stirred for 5 minutes. A solution of ethyl chlorocarbonate (1.63 g) in dry tetrahydrofuran (10.00 ml) was added to the mixture under ice-cooling, and the mixture was stirred at the same temperature for 20 minutes. L-phenylalanine amide hydrochloride and triethylamine (2.25 ml) were added to the mixture, and the mixture was stirred under ice-cooling for 2 hours and under room temperature for one hour, followed by concentration under a reduced pressure. Water was added to the residue, and the insolubles therein were filtered, thoroughly washed with water, and further washed with 50% aqueous ethyl alcohol and 50% ethyl alcohol-ethyl ether, followed by drying, to give N-[trans-4-(t-butoxycarbonylaminomethyl)cyclohexylcarbonyl]-L-phenylalanine amide (I) (4.82 g) as a white powder. This structure was confirmed by NMR spectrum.

4 N hydrogen chloride/1,4-dioxane solution (30 ml) was added to the compound (I) (2.47 g), and the mixture was stirred under room temperature for one hour. The solvent was evaporated under a reduced pressure, and the residue was collected by suction using ethyl ether and washed with ethyl ether to obtain N-[trans-4-aminomethylcyclohexylcarbonyl]-L-phenylalamine amide hydrochloride (2.13 g) as a white powder.

The Trans-4-(t-butoxycarbonyl)aminomethylcyclohexyl carboxylic acid used in the present invention was synthesized according to the following method.

Trans-4-aminomethylcyclohexylcarboxylic acid (15.7 g) was suspended in a mixture (300 ml) of water: 1,4-dioxane=1:1. Triethylamine (45 ml) was added to the suspension, and after the mixture became homogeneous, di-t-butyl dicarbonate (24.0 g) was added at one time under ice-cooling. The ice bath was removed and the mixture was stirred at room temperature for 3 hours, and then extracted with an addition of water (150 ml) and ethyl acetate (150 ml). The aqueous layer was recovered, made weakly acidic with 6N HCl under ice-cooling, and the precipitated oily substance was extracted with ethyl acetate (300 ml). The organic layer was washed with water, and with saturated aqueous sodium chloride and then dried over anhydrous sodium sulfate, followed by evaporation of the solvent under a reduced pressure. The crystalline residue was recrystallized from diethyl ether-hexane to obtain trans-4-(t-butoxycarbonylaminomethyl)cyclohexyl carboxylic acid (24.1 g).

EXAMPLE 2

Synthesis of
N-(4-aminomethylbenzoyl)-L-phenyl-alanineamide hydrochloride (Compound 2)

To a mixture of 4-(t-butoxycarbonylaminomethyl)-benzoic acid (3.77 g), L-phenylalamine amide hydrochloride (3.01 g), triethylamine (2.25 g) and dry dichloromethane (100 ml) 1-ethyl-3-(3-dimethylaminopropyl)-carbodiimide hydrochloride (3.16 g) was added, under ice-cooling, and after cooling for 2 hours, the mixture was stirred under room temperature for 2 hours. The solvent was evaporated under a reduced pressure, water was added to the residue to effect powdering, and the powder was collected by filtration. The powder was washed with 10% aqueous citric acid, water, 5% aqueous sodium hydrogen carbonate, and then water, in this order, followed by drying, to give N-[4-(t-butoxycarbonylaminomethyl)benzoyl]-L-phenylalamine amide (I) (4.41 g). The structure was confirmed by NMR spectrum.

To the compound (I) (2.84 g), 4 N hydrogen chloride/1,4-dioxane solution (35 ml) under room temperature was added and the mixture was stirred at the same temperature for 2 hours. The mixture was concentrated under a reduced pressure, and the residue washed with ethyl ether, followed by filtration to give N-(4-aminomethylbenzoyl)-L-phenylalanine amide hydrochloride (2.32 g) as a white powder.

The 4-(t-butoxycarbonylaminomethyl)benzoic acid used in the present invention was synthesized according to the following method.

After 4-aminomethylbenzoic acid (10 g) and t-butyloxycarbonyloxyimino-2-phenylacetonitrile (19 g) were dissolved in a mixed solution of water-dioxane (200 ml), triethylamine (14 g) was added and the mixture was stirred at room temperature for 12 hours. After the reaction, the solvent was evaporated and then water (100 ml) was added, followed by washing with ethyl acetate. The mixture was made acidic with citric acid, extracted with ethyl acetate, and dried over sodium sulfate. After evaporation of the solvent, the residue was recrystallized from chloroform to obtain 4-(t-butoxycarbonylaminomethyl)benzoic acid (I) (14 g).

EXAMPLE 3

Synthesis of N-(trans-4-aminomethylcyclohexyl-carbonyl)-L-phenylalanine methylamide hydrochloride (Compound 7)

To a mixture of N-(t-butoxycarbonyl)-L-phenylalanine (5.30 g), methylamine hydrochloride (1.53 g), triethylamine (3.00 ml) and dry dichloromethane (50 ml), 1,3-dicyclohexylcarbodiimide (4.12 g) was added at −10° C., and the mixture was stirred for 2 hours and again at room temperature for 2 hours. The precipitates were filtered off, the filtrate was concentrated under a reduced pressure and ethyl acetate was added to the residue, and the insolubles were filtered off. The filtrate was washed with 10% aqueous citric acid, water, 5% aqueous sodium hydrogen carbonate, water, and saturated aqueous sodium chloride, in this order, and dried over anhydrous sodium sulfate. The solids were filtered off, and the filtrate was concentrated under a reduced pressure to give a white powder. The powder was washed with a solvent mixture of isopropyl ether:n-hexane=1:1 to obtain N-(t-butoxycarbonyl)-L-phenylalanine methylamide (I) (1.08 g).

To the compound (I) (2.00 g), 4N hydrogen chloride/1,4-dioxane solution (36 ml) was added, and the mixture was stirred under room temperature for one hour. The solvent was evaporated under a reduced pressure and toluene was added to the residue, followed by reevaporation to give L-phenylalanine methylamide hydrochloride quantitatively as a white powder.

On the other hand, trans-4-(t-butoxycarbonylaminomethyl)cyclohexyl carboxylic acid (203 g) was dissolved in dry tetrahydrofuran (80 ml) and triethylamine (1.19 ml) was added under ice-cooling to the solution, and the solution was stirred for 10 minutes. Subsequently, a solution of ethyl chlorocarbonate (0.85 g) in dry tetrahydrofuran (5 ml) was added and the mixture was further stirred for 20 minutes. The mixture was added to a mixture of the hydrochloride (II) previously obtained, triethylamine (1.19 ml), and N,N-dimethylformamide (5 ml) under ice-cooling, followed by stirring for 2 hours and again under room temperature for 2 hours. The solvent was evaporated under a reduced pressure, the residue was diluted with ice-water, and the precipitates were collected by filtration and washed with water. The product was washed with 10% aqueous citric acid and with water, followed by washing with 50% aqueous ethyl alcohol, 50% ethyl alcohol-ethyl ether, and dried to give N-[trans-4-(t-butoxycarbonylaminomethyl)cyclohexylcarbonyl]-L-phenylalanine methylamide (III) (2.57 g).

To the compound (III) (2.29 g) was added 4N hydrogen chloride/1,4-dioxane solution (23 ml), and the mixture was stirred at room temperature for one hour. The solvent was evaporated under a reduced pressure, and the residue was washed with ethyl ether and filtered to give N-(trans-4-aminomethylcyclohexylcarbonyl)-L-phenylalanine methylamide hydrochloride (2.03 g) as a white powder.

EXAMPLE 4

Synthesis of N-(trans-4-aminomethylcyclohexyl-carbonyl)-L-phenylalanine dimethylamide hydrochloride (Compound 9):

To a solution of N-(t-butoxycarbonyl)-L-phenylalanine (26.5 g), dimethylamine hydrochloride (9.14 g) and 1-ethyl-3-(3-dimethylaminopropyl)carbodiimide hydrochloride (21.0 g) in dry dichloromethane (200 ml), triethylamine (16.50 ml) was added at −10° C. The mixture was stirred at the same temperature for 2 hours, and again at room temperature for 2 hours. Water was added to the reaction mixture to obtain an organic layer, which was washed with 10% aqueous citric acid, water, 5% aqueous sodium hydrogen carbonate, and water, in this order, and dried over anhydrous sodium sulfate. The solids were filtered off, the filtrate was concentrated under a reduced pressure, and the residue was subjected to silica gel column chromatography. From the eluate with n-hexane:ethyl acetate=2:1, N-(butoxycarbonyl)-L-phenylalanine dimethylamide (I) (19.23 g) was obtained as a white powder. This structure was confirmed by NMR spectrum.

To the compound (I) (19.00 g), 4 N hydrogen chloride/1,4-dioxane solution (325 ml) was added under room temperature, and the mixture was stirred at the same temperature for 30 minutes. The mixture was concentrated under a reduced pressure, and L-phenylalanine dimethylamide hydrochloride (II) was obtained quantitatively as a white powder. Subsequently, to a solution of the compound (II), trans-4-(t-butoxycarbonylaminomethyl)cyclohexylcarboxylic acid (16.70 g) and triethylamine (9.75 ml) in dry dichloromethane (200 ml), 1-ethyl-3-(3-dimethylaminopropyl)carbodiimide hydrochloride (13.69 g) was added under ice-cooling, the mixture was stirred for 2 hours, and again stirred at room temperature for 2 hours. To the reaction water was added to obtain an organic layer, which was washed with 10% aqueous citric acid, water, 5% aqueous sodium hydrogen carbonate, and water, in this order, followed by drying over anhydrous sodium sulfate. The solids were filtered off, the filtrate concentrated under a reduced pressure and the residue was washed with diethyl ether, followed by filtration to give N-[trans-4-(t-butoxycarbonylaminomethyl)cyclohexylcarbonyl]-L-phenylalanine dimethylamide (III) (21.90 g). The structure was confirmed by NMR.

To the compound (III) (34.30 g) was added 4N hydrogen chloride/1,4-dioxane solution (400 ml) under room temperature, and the mixture was stirred for 30 minutes. The mixture was concentrated under a reduced pressure, and the residue was washed with diethyl ether, followed by filtration to give N-(trans-4-aminomethyl-cyclohexylcarbonyl)-L-phenylalanine dimethylamide hydrochloride (28.50 g).

EXAMPLE 5

Synthesis of N-(4-guanidinobenzoyl)-L-phenylalanine 4-cis/trans-methylcyclohexylamide hydrochloride (Compound 12)

To a solution of N-(t-butoxycarbonyl)-L-phenylalanine (1 g), triethylamine (2 ml) and dry tetrahydrofuran (30 ml), ethyl chlorocarbonate (0.4 g) were added under ice-cooling, and the mixture was stirred for 30 minutes. To the reaction mixture 4-cis/trans-methylcyclohexylamine (0.25 g) was added, and the mixture was further stirred at room temperature for 10 hours.

After evaporation of the solvent, the residue was extracted with ethyl acetate, washed with water, and dried over sodium sulfate. After evaporation of the solvent, a white powder of N-(t-butoxycarbonyl)-L-phenylalanine 4-cis/trans-methylcyclohexylamide (I) (0.5 g) was obtained. After confirmation by NMR and IR, 4N hydrogen chloride/1,4-dioxane solution (5 ml) was added to the above compound (I) (0.5 g) under ice-cooling, and the mixture was stirred at room temperature for 30 minutes. Hexane (20 ml) was added and the solids precipitated were washed several times with diethyl ether to obtain white solids (0.45 g) of L-phenylalanine 4-cis/trans-methylcyclohexylamide hydrochloride (II). This structure was confirmed by NMR spectrum. To the mixture of 4-guanidino benzoic acid hydrochloride, dry pyridine (3 ml) and 1,3-dicyclohexylcarbodiimide (0.36 g), the above compound (II) was added under ice-cooling, and the mixture was left to stand at room temperature for 12 hours. After a conventional post-treatment, pale yellow solids of N-(4-guanidinobenzoyl)-L-phenylalanine 4-cis/trans-methylcyclohexylamide (III) (0.5 g) were obtained. After confirmation by NMR, the above compound (III) (0.5 g) was added to a saturated sodium hydrogen carbonate solution (10 ml) and the mixture was stirred for 5 minutes, followed by a recovery of the precipitates. After washing several times with water, pale yellow solids of N-(4-guanidinobenzoyl)-L-phenylalanine 4-cis/trans-methylcyclohexylamide carbonate (IV) (0.25 g). After confirmation by IR, the above compound (IV) (0.2 g) was added to a 4N hydrogen chloride/1,4-dioxane solution (1 ml) under ice-cooling, and the mixture was stirred for 20 minutes. Diethyl ether was then added, and the precipitated solids were washed several times with diethyl ether to obtain N-(4-guanidinobenzoyl)-L-phenylalanine 4-cis/transmethylcyclohexylamide hydrochloride (0.15 g) as pale yellow solids.

EXAMPLE 6

Synthesis of N-(trans-4-aminomethylcyclohexyl-carbonyl)-L-phenylalanine 4-carbamoylanilide hydrochloride (Compound 13)

N-(t-butoxycarbonyl)-L-phenylalanine (26.50 g) was dissolved in dry tetrahydrofuran (800 ml), and triethylamine (15 ml) was added under ice-cooling, followed by stirring at the same temperature for 10 minutes. Subsequently, a solution of ethyl chlorocarbonate (10.85 g) in dry tetrahydrofuran (70 ml) was added dropwise over 5 minutes. The mixture was further stirred under ice-cooling for 30 minutes. To the mixture, p-aminobenzamide (13.60 g) was added and the mixture was stirred for 2 hours at the same temperature and again under room temperature for 12 hours. To the above mixture, ice-water (1.4 liter) was added and the insolubles were collected by filtration, thoroughly washed with water, and dried to obtain N-(t-butoxycarbonyl)-L-phenylalanine 4-carbamoylanilide (I) (33.06 g) as a white powder. The structure was confirmed by NMR.

To the compounds (I) (19.15 g) was added dry 1,4-dioxane (50 ml) and 4N hydrogen chloride/1,4-dioxane solution (250 ml), and the mixture was stirred under room temperature for 2 hours. The solvent was removed under a reduced pressure and toluene was added and reevaporated to give L-phenylalanine 4-carbamoylanilide hydrochloride (II) quantitatively as a white powder. On the other hand, trans-4-(t-butoxycarbonylaminomethyl)cyclohexylcarboxylic acid (13.36 g) was dissolved in dry tetrahydrofuran (500 ml), and triethylamine (7.80 ml) was added under ice-cooling, followed by stirring at the same temperature for 10 minutes. Subsequently, a solution of ethyl chlorocarbonate (5.64 g) in dry tetrahydrofuran (50 ml) was added dropwise under ice-cooling for 3 minutes, and the mixture was again stirred at the same temperature for 20 minutes. The above mixture was added to the suspension of the hydrochloride (II) previously obtained and triethylamine (8.53 ml) in N,N-dimethylformamide (150 ml) under ice-cooling, followed by stirring at the same temperature for 2 hours, and under room temperature for 6 hours. Ice-water (1.4 liter) was added and the insolubles were collected by filtration, thoroughly washed with water, and further washed with 10% aqueous citric acid, water 5% aqueous sodium hydrogen carbonate, followed by washing with water at 40° to 50° C., and drying, to give N-[4-trans-(t-butoxycarbonylaminomethyl)cyclohexylcarbonyl]-L-phenylalanine 4-carbamoylanilide (III) (24.63 g). The structure was confirmed by NMR.

To the compounds (III) (24 g), dry 1,4-dioxane (50 ml) and 4 N hydrogen chloride/1,4-dioxane solution (250 ml) was added and the mixture was stirred under room temperature for 2 hours. The solvent was evaporated under a reduced pressure, and the residue was collected by filtration with dichloromethane. This was recrystallized from methyl alcohol:chloroform to obtain N-(trans-4-aminomethylcyclohexylcarbonyl)-L-phenylalanine 4-carbamoylanilide hydrochloride (15.40 g) as a white powder.

EXAMPLE 7

Synthesis of N-(trans-4-aminomethylcyclohexylcarbonyl)-L-phenylalanine 4-hydroxycarbonylanilide hydrochloride (Compound 14)

To a solution of N-[trans-4-(butoxycarbonylaminomethyl)-cyclohexylcarbonyl]-L-phenylalanine 4-ethoxycarbonylanilide (5.51 g) obtained by the same method as used in Example 6, tetrahydrofuran (50 ml) and ethyl alcohol (50 ml), a 2N aqueous sodium hydroxide (12.50 ml) was added and the mixture was stirred under room temperature for 24 hours. The mixture was concentrated under a reduced pressure, and 10% aqueous citric acid was added to the residue under ice-cooling. The insolubles were collected by filtration, thoroughly washed with water, and dried, and N-[trans-4-(t-butoxycarbonylaminomethyl)cyclohexylcarbonyl]-L-phenylalanine 4-hydroxycarbonylanilide (I) (5.13 g) was obtained as a white powder.

To the compound (I) (2.88 g), 4 N hydrogen chloride/1,4-dioxane solution (28 ml) was added and the mixture was stirred under room temperature for 2 hours. The solvent was removed under a reduced pressure, and the residue was collected by filtration with dichloromethane to obtain N-(trans-4-aminomethylcyclohexylcarbonyl)-L-phenylalanine 4-hydroxycarbonylanilide hydrochloride (2.40 g) as a white powder.

EXAMPLE 8

Synthesis of N-(4-aminomethylbenzoyl)-L-phenylalanine 4-acetylanilide hydrochloride (Compound 16)

L-Phenylalanine 4-acetylanilide hydrochloride (I) (0.75 g) was obtained by the same method as used in Example 6.

On the other hand, 4-(t-butoxycarbonylaminomethyl)benzoic acid (0.63 g) and triethylamine (1.0 g) were dissolved in dry tetrahydrofuran (30 ml) and the solution was stirred under ice-cooling for 10 minutes.

Subsequently, a solution of ethyl chlorocarbonate (0.28 g) in dry tetrahydrofuran (2 ml) was added under ice-cooling over 5 minutes, and the mixture was stirred at the same temperature for 60 minutes. The precipitated solids were quickly filtered off, (I) was added to the filtrate, and the mixture was stirred under ice-cooling for 1 hour, and again at room temperature for 12 hours.

After post-treatment in a conventional manner and recrystallization from dichloromethane, N-[4-t-butoxycarbonylaminomethyl)benzoyl]-L-phenylalanine 4-acetylanilide (II) (1.0 g) was obtained.

The compound (II) (1.0 g) was added to a 4 N hydrochloric acid/1,4-dioxane solution (10 ml) and the mixture was stirred at room temperature for 20 minutes.

Diethyl ether was added to precipitate the solids, and after washing several times with diethyl ether, the solids were recrystallized from 2-propanol to give N-(4-aminomethylbenzoyl)-L-phenylalanine 4-acetylanilide hydrochloride (0.50 g).

EXAMPLE 9

Synthesis of N-(trans-4-guanidinomethylcyclohexylcarbonyl)-L-phenylalanine dimethylamide methanesulfonate (Compound 19)

L-Phenylalanine dimethylamide hydrochloride (3.0 g) obtained according to Example 4 and trans-4-guanidinomethylcyclohexylcarboxylic acid (3.09 g) were dissolved in dry pyridine (30 ml), and 1,3-dicyclohexylcarbodiimide (2.97 g) was added, followed by stirring at room temperature for 24 hours.

After completion of the reaction, the insolubles were filtered off. The filtrate was concentrated under a reduced pressure, and the concentrated was mixed with saturated sodium hydrogen carbonate solution (30 ml) and then stirred at room temperature for 24 hours. The insolubles were collected by filtration, washed with water, and then dried.

To the solid suspended in methanol (10 ml), methanesulfonic acid (12.6 g) was added under room temperature, and the mixture was stirred for 15 minutes.

To the mixture, ethyl ether was added and the precipitates formed were collected by filtration and washed with ethyl ether to give N-(trans-4-guanidinomethylcyclohexylcarbonyl)-L-phenylalanine dimethylamide methansulfonate (2.1 g).

EXAMPLE 10

Synthesis of Ethyl N-N-(trans-4-aminomethylcyclohexylcarbonyl)-L-phenylalanyl-L-serinate hydrochloride (Compound 20)

To a solution of N-(t-butoxycarbonyl)-L-phenylalanine (3.98 g), ethyl L-serinate (2.54 g) and triethylamine (2.25 ml) in dry dichloromethane (100 ml), 1-ethyl-3-(3-dimethylaminopropyl)-carbodiimide hydrochloride (3.16 g) was added under ice-cooling, followed by stirring at the same temperature for 2 hours, and again under room temperature for 2 hours. To the mixture, water (100 ml) was added to obtain an organic layer, which was further washed with 10% aqueous citric acid, water, 5% aqueous sodium hydrogen carbonate, water, and then saturated aqueous sodium chloride, followed by drying over anhydrous sodium sulfate. The solids were filtered off, and the filtrate was concentrated under a reduced pressure to give ethyl N-[N-(t-butoxycarbonyl)-L-phenylalanyl]-L-serinate (I) (3.67 g) as a white powder. The structure was confirmed by NMR spectrum.

To the compound (I) (2.66 g), 4N hydrogen chloride/1,4-dioxane solution (35 ml) was added at room temperature, and the mixture was stirred at the same temperature for one hour. The mixture was concentrated under a reduced pressure, toluene was added to the residue and then reevaporated to give ethyl N-(L-phenylalanyl)-L-serinate hydrochloride (II) quantitatively as a white powder. To this product, trans-4-(t-butoxycarbonylaminomethyl)cyclohexylcarboxylic acid (1.80 g), triethylamine (1.05 g), and dry dichloromethane (50 ml) were added. Subsequently, under ice-cooling, 1-ethyl-3-(3-aminopropyl)carbodiimide hydrochloride (1.47 g) was added to the mixture, the mixture was stirred at the same temperature for 2 hours, and again under room temperature for 2 hours. Ice-water was added and the precipitated gel-like substance was collected by filtration, washed with water, 10% aqueous citric acid, water, 5% aqueous sodium hydrogen carbonate and again with water, to obtain a powdery substance which was dried to give ethyl N-[N-(trans-4-(t-butoxycarbonylaminomethyl)cyclohexylcarbonyl-L-phenylalanyl]-L-serinate (III) (1.73 g). The structure was confirmed by NMR spectrum.

The compound (III) (1.70 g) was treated similarly with 4N hydrogen chloride/1,4-dioxane solution (17 ml) to obtain ethyl N-[N-(trans-4-aminomethylcyclohexyl-carbonyl)-L-phenylalanyl]-L-serinate hydrochloride (1.47 g) as white powder.

EXAMPLE 11

Synthesis of N-(4-amidinobenzoyl)-L-phenylalanine dimethylamide hydroiodide (Compound 22)

To a mixture of L-phenylalanine dimethylamide hydrochloride (5.15 g), p-cyanobenzoic acid (3.30 g) and triethylamine (3.37 ml), to which dry dichloromethane (100 ml) was added, 1-ethyl-3-(3-diaminopropyl)carbodiimide hydrochloride (4.74 g) was added under ice-cooling and the mixture was stirred at the same temperature for 2 hours and again under room temperature for 2 hours. Water was added to obtain an organic layer, which was washed with 10% aqueous citric acid, water, 5% aqueous sodium hydrogen carbonate, and water, in this order, and dried over anhydrous sodium sulfate. The solids were filtered off, and the filtrate was concentrated under a reduced pressure, and N-(4-cyanobenzoyl)-L-phenylalanine dimethylamide (I) (3.96 g) was obtained from the reside as a white powder.

Hydrogen sulfide gas was reacted with a mixture of the compound (I) (3.80 g), pyridine (4.00 ml) and triethylamine (2.00 ml) for 2 hours under ice-cooling, and the mixture was left to stand for 2 days. To the reaction mixture, 10% aqueous citric acid was added, the insolubles were collected by filtration, and washed twice with 10% aqueous citric acid. The product was then thoroughly washed with water and dried to obtain a thioamide (II) (3.77 g).

To the compound (II) (3.65 g), acetone (100 ml) and methyl iodide (29.19 g) was added under room temperature, followed by stirring at the same temperature for 12 hours. The mixture was concentrated under a reduced pressure, and the residue was collected by filtration with diethyl ether to obtain an iminothioester (III) (4.15 g).

A solution of the compound (III) (4.00 g) and ammonium acetate (0.81 g) in ethyl alcohol (100 ml) was stirred at 55° C. to 60° C. The mixture was concentrated under a reduced pressure, and the residue was washed with diethyl ether and then collected by filtration to obtain N-(4-amidinobenzoyl)-L-phenylalanine dimethylamide hydroiodide (3.47 g).

EXAMPLE 12

Synthesis of N-(trans-4-aminomethylcyclohexylcarbonyl)-L-phenylalanine 4-methylcarbamoylanilide hydrochloride (Compound 23)

To a mixture of N-[trans-4-(t-butoxycarbonylaminomethyl)cyclohexylcarbonyl]-L-phenylalanine 4-hydroxycarbonylanilide (5.23 g) obtained according to the same method as in Example 6, methylamine hydrochloride (2.03 g), 1-ethyl-3-(3-dimetyl aminopropyl)carbodiimide hydrochloride (3.83 g) and dry dichloromethane (100 ml), triethylamine (4.50 ml) was added under ice-cooling, and the mixture was stirred at the same temperature for 2 hours and again under room temperature for 3 hours. The mixture was concentrated under a reduced pressure and water was added to the residue to form a powder, which was then collected by filtration. After a thorough washing with water, the powder was washed with 10% aqueous citric acid, water, 5% aqueous sodium hydrogen carbonate and water in this order, followed by drying. N-[trans-4-(t-butoxycarbonylaminomethyl)cyclohexylcarbonyl]-L-phenylalanine 4-methylcarbamoylanilide (I) (4.08 g) was obtained as a white powder.

To the compound (I) (2.68 g), 4N hydrogen chloride/1,4-dioxane solution (25 ml) was added and the mixture was stirred under room temperature for 2 hours. The solvent was evaporated under a reduced pressure, and the residue was washed with dichloromethane and then collected by filtration to obtain N-(trans-4-aminomethylcyclohexylcarbonyl)-L-phenylalanine 4-methylcarbamoylanilide hydrochloride (2.32 g).

EXAMPLE 13

Synthesis of N-(4-aminomethylbenzoyl)-L-phenylalanine 4-carbamoylanilide hydrochloride (Compound 27)

N-(t-butoxycarbonyl)-L-phenylalanine (10.0 g), p-aminobenzamide (4.40 g) and triethylamine (3.25 g) were dissolved in dry methylene chloride (40 ml), 1-ethyl-3-(3-dimethylaminopropyl)carbodiimide hydrochloride (6.80 g) was added to the solution under ice-cooling, and the mixture was stirred under room temperature for 8 hours. .After completion of the reaction, a post-treatment was conducted according to the conventional method to give N-(t-butoxycarbonyl)-L-phenylalanine 4-carbamoylanilide (I) (6.3 g) as a white powder.

The compound (I) (6.3 g) was added into 4 N hydrogen chloride/1,4-dioxane (22 ml) under room temperature, and the mixture was stirred at room temperature for 30 minutes. After completion of the reaction, ethyl ether was added to effect precipitation, followed by filtration to give L-phenylalanine 4-carbamoylanilide hydrochloride (II) (3.9 g) as a white powder.

This product, 4-(t-butoxycarbonylaminomethyl)benzoic acid (3.06 g) and triethylamine (2.83 g) was dissolved in dry methylene chloride (30 ml), and 1-ethyl-3-(3-dimethylaminopropyl)-carbodiimide hydrochloride (2.57 g) was added under ice-cooling, followed by stirring under room temperature for 8 hours.

After completion of the reaction, a conventional post-treatment was conducted, and a recrystallization aminomethyl)benzoyl]-L-phenylalanine 4-carbamoylanilide (III) (3.8 g) as a white powder.

The compound (III) was reacted with 4N hydrogen chloride/1,4-dioxane solution (8 ml) followed by a post-treatment to give N-(4-aminomethylbenzoyl)-L-phenylalanine 4-carbamoylanilide hydrochloride (2.8 g) as a white powder.

EXAMPLE 14

Synthesis of N-(4-amidinobenzoyl)-L-phenylalanine 4-carbamoylanilide methanesulfonate (Compound 28)

To a mixture of L-phenylalanine 4-carbamoylanilide hydrochloride (2.40 g) obtained according to Example 6, 4-amidinobenzoic acid hydroiodide (2.19 g), triethylamine (1.03 ml) and dry pyridine (30 ml), 1-ethyl-3-(3-diaminopropyl)carbodiimide hydrochloride (1.58 g) was added under ice-cooling, and the mixture was stirred for 2 hours, and then under room temperature for 12 hours. To the mixture, ice-water was added and the insolubles were collected by filtration, and thoroughly washed with water, followed by throwing into a 5% aqueous sodium hydrogen carbonate and stirring. After 6 hours, the insolubles were collected by filtration and thoroughly washed with water, followed by drying to obtain a pale yellow powder. The powder was suspended in methyl alcohol and methanesulfonic acid (0.60 g) was added to the suspension. The mixture was stirred under room temperature for 6 hours, concentrated under a reduced pressure, washed with ethyl ether, and the residue was collected by filtration to give N-(4-amidinobenzoyl)-L-phenylalanine 4-carbamoylanilide methanesulfonate (1.12 g) as a pale yellow powder.

EXAMPLE 15

Synthesis of N-(trans-4-aminomethylcyclohexylcarbonyl)-3-phenoxy-DL-phenylalanine 4-acetylanilide hydrochloride (Compound 2)

(1) Into thionyl chloride (520 g), 3-phenoxybenzyl alcohol (200 g) was added, dropwise over 1 hour, under ice-cooling. Then, the mixture was stirred at room temperature for 24 hours and thionyl chloride was evaporated under a reduced pressure. To the residue, toluene (500 ml) was added, and after reevaporation, the yellow residual oily product was purified by distillation to obtain 180.5 g of a colorless oily product (bp. 122°–124° C./1.5 mmHg). From various spectra data, this compound was confirmed to be 3-phenoxybenzyl chloride (II).

(2) To a solution of sodium ethoxide prepared from anhydrous ethanol (one liter) and sodium (15 g), ethylacetoamide malonate (140 g) was added to carry out the reaction under an ethanol reflux for 15 minutes. The compound (II) (141.5 g) synthesized in (1) at 80° C. was added dropwise to the solution over 15 minutes, and the reaction was then carried out under an ethanol reflux for 6 hours and after cooling, ethanol was evaporated, followed by an extraction of the residue with dichloromethane. The organic layer was thoroughly washed with water and dried, and the solvent was evaporated. Thereafter, the residue was recrystallized from diethyl ether/n-hexane to obtain 209.4 g of colorless prisms. The crystal was identified from various spectra data to be ethyl 2-acetamido-2-carboethoxy-3-(3-phenoxyphenyl)propionate (III).

NMR (CDCl$_3$, TMS) δ:1.24 (6H, t), 1.96 (3H, s), 3.58 (2H, s), 4.06–4.30 (5H, m), 6.52–7.30 (9H, m).

(3) The compound (III) (205 g) obtained in (2) was allowed to react with 48% hydrobromic acid solution (500 ml) under a heating reflux for 7 hours. After cooling, conc. ammonia water was added under ice-cooling to adjust the pH to 6.5. Ice-cooling was continued, and the crystals precipitated 2 hours later were collected by filtration, washed with cold water, and then with acetone and diethyl ether, followed by drying, to give a white powder (138 g). From various spectra data, this compound was confirmed to be 3-phenoxy-DL-phenylalanine (IV).

(4) The compound (IV) (77.1 g) obtained in (3) was suspended in a solution of 1,4-dioxane:water=1:1 (450 ml) and triethylamine (143 ml) was added thereto. After 15 minutes, di-t-butyl dicarbonate (72 g) was added under ice-cooling to the solution, and the mixture was stirred under ice-cooling for one hour and then at room temperature for 2 hours. After completion of the reaction, ethyl acetate (500 ml) and water (500 ml) were added to effect extraction, whereby an aqueous layer was obtained. To the aqueous layer, citric acid was added under ice-cooling to make the pH weakly acidic, and the oily substance precipitated was extracted with ethyl acetate (500 ml). The organic layer was washed with water, dried, and the solvent then evaporated under a reduced pressure. The residue was crystallized from diethyl ether/n-hexane and then recrystallized to give white prisms (90.4 g). This compound was identified from various spectra data to be N-(t-butoxycarbonyl)-3-phenoxy-DL-phenylalanine (I).

NMR (CDCl$_3$) δ:1.30–1.48 (9H, m), 2.70–3.24 (2H, m), 4.30–4.70 (1H, broad), 4.90–5.04 (1H, broad), 6.80–7.35 (9H, m), 9.00–9.38 (1H, broad).

(5) N-(t-butoxycarbonyl)-3-phenoxy-DL-phenylalanine (I) (7.42 g) obtained in (4) was dissolved in dry tetrahydrofuran (80 ml), triethylamine (3 ml) was added to the solution, and further, ethyl chloroformate (2.40 g) was added under ice-cooling, followed by stirring for 30 minutes. To the solution, 4-acetylanilide (2.70 g) was added and the mixture was stirred under room temperature for 10 hours. To the reaction mixture, ice-water (300 ml) was added, and the crystalline substance precipitated was collected by filtration, thoroughly washed with water, and then dried to obtain N-(t-butoxycarbonyl)-3-phenoxy-DL-phenylalanine 4-acetylanilide (II) 7.07 g) as a white powder. The structure was confirmed by IR and NMR.

To the above compound (II) (2.29 g), 4N hydrogen chloride/1,4-dioxane solution (30 ml) was added under ice-cooling, and after the ice bath was removed, the mixture was stirred under room temperature for 30 minutes. To the solution, diethyl ether (300 ml) was added, and the crystalline substance precipitated was collected by filtration, washed with diethyl ether, and then dried under a reduced pressure to obtain quantitatively 3-phenoxy-DL-phenylalanine 4-acetylanilide hydrochloride (III).

On the other hand, trans-4-(t-butoxycarbonylaminomethyl)cyclohexylcarboxylic acid (1.62 g) was dissolved in dry tetrahydrofuran (50 ml) and N,N-dimethylformamide (20 ml), triethylamine (0.96 ml) was added, and a solution of ethyl chlorocarbonate (0.76 g) in dry tetrahydrofuran (2 ml) was added, followed by stirring for 30 minutes. To the solution, the previous hydrochloride (III) and triethylamine (2 ml) was added, and the mixture was stirred under room temperature for 3 hours. Ice-water (200 ml) was added to the reaction mixture, and the precipitated crystalline substance was collected by filtration, thoroughly washed with water, and dried to obtain 2.62 g of N-[trans-4-(t-butoxycarbonylaminomethyl)cyclohexylcarbonyl]-3-phenoxy-DL-phenylalanine 4-acetylanilide (IV). The NMR data did not contradict this result.

To the above compound (IV) (2.60 g), 4N hydrogen chloride/1,4-dioxane solution (25 ml) was added under ice-cooling, and the mixture was stirred under room temperature for 30 minutes. Diethyl ether (100 ml) was added to the mixture, and the precipitated crystalline substance was collected by filtration, washed with diethyl ether, and dried under a reduced pressure to obtain N-(trans-4-aminomethylcyclohexylcarbonyl)- 3-phenoxy-DL-phenylalanine 4-acetylanilide hydrochloride (V) (1.90 g) as a white powder.

The phenylalanine derivative having the formula (I), or a pharmacologically acceptable salt thereof, of the present invention as the therapeutical agent for a peptic ulcer can be used alone or after mixing with an appropriate pharmaceutical additive, with a conventional excipient, in various dosage forms according to a conventional means used for such a preparation, such as a powder, granules, grains, tablets, capsules, a syrup, or a liquid, for oral administration, or into a dosage for injection for parenteral administration.

According to the present invention, any conventional carrier can be used for the preparation of the present anti-peptic ulcer composition. Examples of such carrier are crystalline cellulose, lactose, sucrose, glucose, fructose, sorbitol, mannitol, dextrin, carboxymethylcellulose, carboxymethylcellulose sodium, methylcellulose, ethylcellolose, hydroxypropylcellulose, hydroxypropylmethylcellulose, sodium alginate, tragacanth, acacia, gelatin, aluminum silicate, magnesium silicate, magnesium metaluminosilicate, aluminum hydroxide, anhydrous silicic acid, calcium sulfate, calcium carbonate, dibasic calcium phosphate, dibasic sodium phosphate, magnesium oxide, corn starch, potato starch, wheat starch, hydroxypropyl-starch, carboxymethylcellulose calcium, stearic acid, magnesium stearate, calcium stearate, talc, glyceryl monostearate, sucrose esters of fatty acids and cyclodextrins.

There are no critical limitations to the amounts of the active ingredient and the carrier in the present anti-peptic ulcer composition, i.e., these amounts may widely vary depending upon, for example, the type of the composition, but generally speaking, the active ingredient may be included in an amount of 1% to 70% by weight, preferably 1% to 50% by weight, in the composition, and the carrier may be included in an amount of 99% to 30% by weight, preferably 99% to 50% by weight in the composition.

The administered dose may be suitably determined depending on the age, body weight, and severity of the disease of the patient, but is generally administered at a dose within the range of 10 mg to 5,000 mg per day for an adult human in the case of an oral administration, and 1 mg to 1,000 mg per day for an adult human in the case of a parenteral administration.

The compound of the present invention can be used as an anti-ulcer agent, for example, according to the following recipes.

EXAMPLE 16

Tablet

| | |
|---|---|
| (1) Compound | 50 g |
| (2) Lactose | 50 g |
| (3) Corn starch | 29 g |
| (4) Magnesium stearate | 1 g |
| | 180 g per 1000 tablets |

(1), (2) and 17 g of corn starch was kneaded and granulated together with a paste prepared from 7 g of corn starch, and to the granules were added 5 g of corn starch and (4). The mixture was compressed by a compression tabletting machine to prepare 1,000 tablets with a diameter of 7 mm, each tablet containing 50 mg of (1).

EXAMPLE 17

Capsule

| | |
|---|---|
| (1) Compound | 50 g |
| (2) Lactose | 100 g |
| (3) Crystalline cellulose | 45 g |
| (4) Magnesium stearate | 5 g |
| | 200 g per 1000 capsules |

All the components were kneaded and filled into 1000 gelatin capsules No. 8 to prepare capsules containing 50 mg of (1) per capsule.

That the phenylalanine derivative having the formula (I) or the pharmacologically acceptable salts thereof of the present invention is effective for the therapy of a peptic ulcer can be recognized from the pharmacological actions thereof, as shown below, against a hydrochloric acid ulcer or a restrictive water immersion stress ulcer, which are experimental ulcers.

(1) Action against hydrochloric acid ulcer

Wistar-strain male rats (weight 180 g, 6 to 7 rats per group) were starved for 18 hours and left without water for 4 hours before the test.

The test drug was formed into an aqueous solution or suspended in an aqueous solution of 0.5% carboxymethyl cellulose and administered orally at a volume of 0.5 ml/100 g, and 30 minutes after administration, 1 ml of 0.6 N-HCl was orally administered. One hour after the administration, the stomach was excised and injected with 5 ml of 5% formalin solution. After the formalin fixation for 10 min., the stomach was cut open along the greater curvature, and the area ($mm^2$) of an ulcer generated at the corpus of stomach was measured.

The total sum of the area of ulcer generated per rat was compared with that of the control group. The control group was administered with water or a 0.5% aqueous carboxymethyl cellulose solution. The Ulcer Index was determined as the inhibition ratio (%).

The experimental results were as shown in Table 2.

(2) Action against restrictive water immersion stress ulcer

Wistar-strain male rats (weight 180 g, 6 to 8 rats per group) were starved for 18 hours before the test. The test drug was administered orally by the same method as used in (1). Thirty minutes after the administration, the rats were placed in a restrictive stress cage, and immersed to the xiphoideus process of the rat in water of 23° C.

After the loading stress for 7 hours, the stomach was excised and, fixed in formalin by the same method as used in (1), and the length (mm) of the ulcer was measured. The total length of an ulcer generated per rat was compared with that of the control group. An Ulcer Index was determined as the inhibition ratio (%).

The experimental results were as shown in Table 3.

That the compound selected from the compounds represented in the above formula inhibited ulcer formation through a potent defense factor potentiating action against the hydrochloric acid ulcer of (1) is shown by the results in Table 3.

Also, that the compound selected from the compounds represented in the above formula clearly inhibited the restrictive water immersion stress ulcer which concerns an offense factor inhibiting effect is shown by the results in Table 3.

(3) Acute toxicity test

ICR-strain male mice (weight 30 g, 6 mice per group) were starved for 5 hours before the test. The test drug was formed into an aqueous solution, or suspended in 0.5% aqueous carboxymethyl cellulose solution, and administered at a volume of 0.2 ml/10 g.

General symptoms and mortality after the administration were observed for 7 days.

In the compounds selected from among the compounds listed in Table 1, there was no death example in administration of 2000 mg/kg. As any toxicological symptoms was not observed, the compounds were estimated to be extremely safe drugs with an $LD_{50}$ value of 2000 mg/kg.

TABLE 2

| Compound No. | Anti-ulcer action (hydrochloric acid ulcer model: 100 mg/kg peroral administration) (Inhibition rate against non-administered animal) |
|---|---|
| 1 | 77.1% |
| 2 | 58.2 |
| 3 | 91.4 |
| 4 | 71.4 |
| 5 | 53.3 |
| 6 | 77.4 |
| 7 | 52.6 |
| 8 | 73.2 |
| 9 | 73.6 |
| 10 | 60.4 |
| 11 | 68.4 |
| 12 | 89.4 |
| 13 | 85.7 |
| 14 | 74.8 |
| 15 | 73.1 |
| 16 | 96.6 |
| 17 | 57.5 |
| 18 | 89.2 |

TABLE 2-continued

| Compound No. | Anti-ulcer action (hydrochloric acid ulcer model: 100 mg/kg peroral administration) (Inhibition rate against non-administered animal) |
|---|---|
| 19 | 52.5 |
| 20 | 54.3 |
| 21 | 89.8 |
| 22 | 86.0 |
| 23 | 79.9 |
| 24 | 82.6 |
| 25 | 57.3 |
| 26 | 80.8 |
| 27 | 78.1 |
| 28 | 69.8 |
| 29 | 81.0 |
| 30 | 67.5 |
| 31 | 92.3 |
| 32 | 86.4 |

TABLE 3

| Compound No. | Anti-ulcer action (stress ulcer: 100 mg/kg peroral administration) (Inhibition rate) against non-administered animal |
|---|---|
| 1 | 88.2% |
| 3 | 52.2 |
| 4 | 74.6 |
| 5 | 76.0 |
| 8 | 65.0 |
| 9 | 77.6 |
| 10 | 86.1 |
| 11 | 85.2 |
| 12 | 65.8 |
| 13 | 64.8 |
| 15 | 76.4 |
| 20 | 70.0 |
| 22 | 76.2 |
| 24 | 70.6 |
| 28 | 57.4 |
| 29 | 83.7 |
| 31 | 60.0 |
| 32 | 67.4 |

We claim:
1. An anti-peptic ulcer composition comprising, as an active ingredient, a therapeutically effective amount of a compound having the formula (I):

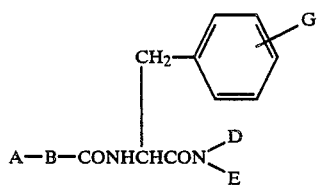

wherein A represents $H_2NCH_2-$,

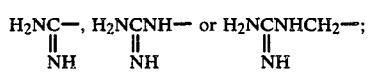

B represents

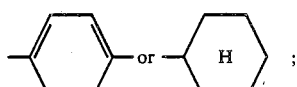

D and E each independently represent H, R, $-R'-CO_2R$, $-R'(OH)CO_2R$,

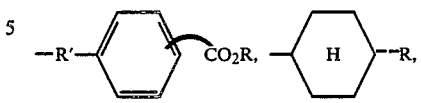

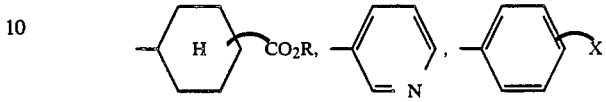

or D and E with the nitrogen to which they are bonded may form a piperidino ring which is substituted with a $CO_2R$ wherein x represents H, $CONR_2$, $CONHR$, $CONH_2$, $CO_2H$, $CO_2R$, or $COR$; $R'$ represents a lower alkylene group and R represents a lower alkyl group; G represents H,

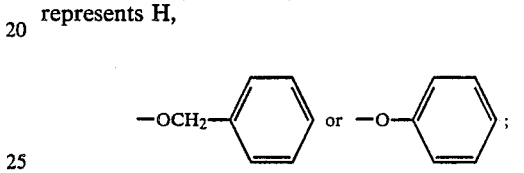

or a pharmaceutically acceptable salt thereof, and a pharmaceutically acceptable carrier.

2. An anti-peptic ulcer composition as claimed in claim 1, wherein said pharmaceutically acceptable salt is at least one salt selected from the group consisting of hydrochloride, hydrobromide, hydroiodide, sulfate, nitrate, phosphate, oxalate, succinate, glycolate, malate, citrate, lactate, benzene sulfonate, toluene sulfonate, and methane sulfonate.

3. An anti-peptic ulcer composition as claimed in claim 1, wherein said compound is selected from the group consisting of those having

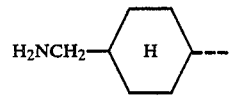

or

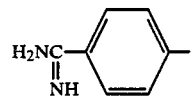

as A—B— in the formula (I); H,—R,

$-R'CO_2R$ as D and E, respectively; and G is H.

4. An anti-peptic ulcer composition as claimed in claim 1, wherein said compound is N-(trans-4-aminomethyl cyclohexylcarbonyl)-L-phenylalanine 4-amino-carbamoylanilide hydrochloride.

5. An anti-peptic ulcer composition as claimed in claim 1, wherein said compound is N-(trans-4-aminomethyl cyclohexylcarbonyl)-L-phenylalanine 4-hydroxycarbonylanilide hydrochloride.

6. An anti-peptic ulcer composition as claimed in claim 1, wherein said compound is N-(4-amidinobenzoyl)-L-phenylalanine dimethylamide hydrochloride.

7. An anti-peptic ulcer composition as claimed in claim 1, wherein said compound is N-(4-aminomethyl cyclohexylcarbonyl)-L-phenylalanine 4-ethoxycarbonyl piperidinoamide hydrochloride.

8. An anti-peptic ulcer composition as claimed in claim 1, wherein said compound is N-(trans-4-aminomethylcyclohexylcarbonyl)-L-phenylalanine amide hydrochloride.

9. A method for treating a peptic ulcer in a patient in need thereof comprising administering thereto a therapeutically effective amount of a compound having the formula (I) defined in claim 1 or a pharmaceutically acceptable salt thereof.

* * * * *